United States Patent
Solomon et al.

(10) Patent No.: US 9,504,493 B2
(45) Date of Patent: *Nov. 29, 2016

(54) SKULL CLAMP SYSTEM WITH PRESSURE LIMITED AND ALARM SYSTEMS

(71) Applicants: Clifford T. Solomon, Severna Park, MD (US); Theodore C. Solomon, Hampstead, MD (US)

(72) Inventors: Clifford T. Solomon, Severna Park, MD (US); Theodore C. Solomon, Hampstead, MD (US)

( * ) Notice: Subject to any disclaimer, the term of this patent is extended or adjusted under 35 U.S.C. 154(b) by 126 days.

This patent is subject to a terminal disclaimer.

(21) Appl. No.: 14/341,061

(22) Filed: Jul. 25, 2014

(65) Prior Publication Data

US 2014/0336647 A1    Nov. 13, 2014

Related U.S. Application Data

(63) Continuation of application No. 13/526,187, filed on Jun. 18, 2012, now Pat. No. 8,801,711.

(60) Provisional application No. 61/497,800, filed on Jun. 16, 2011.

(51) Int. Cl.
*A61B 17/00* (2006.01)
*A61B 17/64* (2006.01)
*A61B 17/62* (2006.01)

(52) U.S. Cl.
CPC .......... *A61B 17/6433* (2013.01); *A61B 17/62* (2013.01); *A61B 17/6408* (2013.01); *A61B 90/14* (2016.02); *A61B 2017/00022* (2013.01); *A61B 2017/00115* (2013.01)

(58) Field of Classification Search
CPC .............. A61B 17/62; A61B 17/6433; A61B 2017/00115
See application file for complete search history.

(56) References Cited

U.S. PATENT DOCUMENTS

| | | | |
|---|---|---|---|
| 3,357,431 A | 12/1967 | Newell | |
| 4,132,224 A | 1/1979 | Randolph | |
| 4,813,435 A | 3/1989 | Arms | |
| 4,838,264 A | 6/1989 | Bremer et al. | |
| 5,147,287 A | 9/1992 | Jewell et al. | |
| 5,289,826 A | 3/1994 | Kovacevic | |
| 5,347,894 A | 9/1994 | Fischer | |
| 5,537,704 A | 7/1996 | Dinkler | |
| 5,879,281 A | 3/1999 | Ein-Gal | |
| 5,961,528 A | 10/1999 | Birk et al. | |
| 6,416,520 B1 * | 7/2002 | Kynast ................. | A61B 19/201 606/130 |
| 7,311,027 B1 | 12/2007 | Tatsuno | |
| 7,458,282 B1 | 12/2008 | Wuester et al. | |
| 7,507,244 B2 | 3/2009 | Dinkler | |
| 7,730,563 B1 | 6/2010 | Sklar et al. | |
| 8,287,537 B2 | 10/2012 | Dinkler, II | |
| 8,801,711 B2 * | 8/2014 | Solomon ................. | A61B 17/62 606/59 |
| 2009/0030359 A1 | 1/2009 | Wikenheiser et al. | |
| 2009/0306662 A1 | 12/2009 | Dinkler, II | |

(Continued)

*Primary Examiner* — Ellen C Hammond
(74) *Attorney, Agent, or Firm* — Seed IP Law Group LLP

(57) ABSTRACT

The skull clamp system with pressure limiting and alarm systems includes at least one and preferably multiple inwardly power driven immobilizing pins adjustably engaging the skull of a patient. The pin power drive systems includes at least one sensor capable of sensing the degree of back pressure on the pin from contact of the pin against the bone of the patient, the sensor being capable of signaling the drive system to stop when the sensor detects a preselected degree of back pressure. The sensor is also capable of signaling an alarm to warn of any reduction of pressure applied to the pins that might result from pin slippage.

9 Claims, 6 Drawing Sheets

(56) References Cited

U.S. PATENT DOCUMENTS

| | | |
|---|---|---|
| 2010/0217280 A1 | 8/2010 | Schuele et al. |
| 2010/0286711 A1 | 11/2010 | Doyle |
| 2013/0190604 A1 | 7/2013 | Moffatt |
| 2013/0324834 A1 | 12/2013 | Majewski et al. |

\* cited by examiner

SKULL CLAMP SYSTEM WITH PRESSURE LIMITED AND ALARM SYSTEMS

CROSS-REFERENCE TO RELATED APPLICATIONS

This application is a continuation of U.S. Ser. No. 13/526,187, filed Jun. 18, 2012, which claims the benefit of U.S. Provisional Patent Application Ser. No. 61/497,800, filed Jun. 16, 2011, which are herein incorporated by reference in their entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

1. Field of the Invention

The present invention relates to devices used in surgical and medical treatment practices, and particularly to a skull clamp device for immobilizing the skull. The device is particularly useful in immobilizing the skull during neurosurgical procedures while providing a sensor safety system for limiting the pressure exerted on the skull by the clamp and providing an alert to the medical team of any potentially hazardous application of clamp pressure or any loosening or slippage of the skull clamp device.

2. Description of the Related Art

There are many medical situations in which it is absolutely vital to immobilize the head of a patient receiving treatment. One common example is during neurosurgery or other cranial surgery, during which the head of the patient must be completely immobilized due to the extremely delicate nature of the operation. Another example is when a neck injury patient is placed in traction to immobilize and protect the patient from further injury while promoting healing.

Various devices for immobilizing the skull have been developed in the past. A well-known example of such a device is the Mayfield skull clamp that is omen used during neurosurgery. This device includes a pair of contact points extending inwardly from an articulating frame on one side of the device, with a third adjustable contact point extending inwardly from the opposite side. The contact points are sharpened pins that penetrate the flesh and engage the outer layer of bone of the skull, and when properly positioned serve to absolutely immobilize the skull relative to the clamp. The clamp itself is adjustably mounted with secure position locking elements on to the structure of an operating table or other patient support structure, thereby absolutely immobilizing the head of the patient during the surgical procedure.

The above-described device is exemplary of other conventionally used cranial immobilizing devices that are well known in the art. These early cranial immobilizing devices present various problems, with one obviously being the potential hazard of manually over-tightening the clamp on to the skull of the patient. This conventional practice of the surgeon manually tightening the skull clamp on to the skull of a patient with the amount of pressure exerted by the clamp pins against the skull being controlled only by the tactile feedback sensed by the surgeon is potentially very dangerous. In many instances the surgeon or other medical practitioner might unintentionally apply too much pressure to the skull as he or she manually tightens the threaded adjustment screw(s) to drive the pin(s) into the bone resulting in an unintentional fracture of the bone. It is critical that the pins be set sufficiently deeply into the outer layer of the bone to completely immobilize the skull for neurosurgery and other cranial procedures without overstressing the bone and causing a skull fracture. The difference between the tactile feedback from applying too little pressure or too much pressure in securing the pins to the skull can be exceedingly small in certain instances. The amount of pressure applied in securing the pins into the outer layer of the skull is complicated by the wide diversity in bone thickness for different patients and even more so by the varied perception of pin pressure against the skull as sensed by individual surgeons during the exertion of manually operation of the clamping devices. Thus, the success of the procedure is completely dependent upon the individual skill level of the surgeon who must manually apply a sufficient but safe amount of penetrating pressure of the pins against the outer layer of the skull. A misjudgement about the amount of pressure to apply in driving the pins into the outer layer of the bone can easily result in a skull fracture, which creates an unnecessary hazard for the patient.

It often occurs that the pins may seem initially to be correctly set and secured into the outer portion of the bone; however, during the course of the surgery some slippage of the pins from their initial position on the skull may occur. When slippage of the connection of the pin to the skull does occur, the skull might move slightly with potentially disastrous results.

There is therefore a need for a skull clamp that can be attached to a patient with improved safety and reliability having an automated capability to control the penetrating pressure of the pin against the skull and a sensor/alarm system that if necessary can instantaneously stop the pin penetration into the skull while alerting the surgeon. A need exists for a skull clamp that is also capable of initiating an alarm if a properly set pin later slips from its position in the bone. Thus a skull clamp system with pressure limiting and alarm systems solving the aforementioned problems is desired.

SUMMARY OF THE INVENTION

The skull clamp system with pressure limiting and alarm systems comprises a skull support clamp having at least one but preferably multiple skull immobilizing pins projecting inwardly therefrom to adjustably engage and immobilize the skull of a patient. The skull support clamp includes at least one pin that is connected to a powered drive system but preferably will include four pins that are motor driven into a secure connection with the skull of a patient. The pins can be automatically and selectively driven into the outer portion of the bone using a powered drive system subject to the control of a preset back pressure limitation for the pins. Preferably the powered drive system is a motorized drive system. An electrical motor drive system is preferred; however, any other drive system such as pneumatic or hydraulic would could also effective serve to provide a powered or motorized drive system. The pins are designed to penetrate into the outer portion of the bone without rotating thus eliminating torsional forces being transmitted from the pin to the contact points on the bone. To avoid potentially destructive torque being applied to the pin-bone contact points, the pins are preferably driven into the outer layer of the bone by a linear directed force rather than a conventional rotationally directed force. At least the tips of the pins that will engage the scalp and skull of the patient can be treated with a suitable antibiotic to reduce the chance of a resulting infection at the contact site. The tips of the pins can also be treated with a blood-clotting agent to minimize bleeding at the pin-skull contact site.

The drive system provided for the pins can include a digital display to indicate to the surgeon, the amount of pressure being applied by the pin against the skull. This important information can also be transmitted by direct wired or by wireless means to a remote monitoring system for observation by another member of the surgical team assisting the surgeon. The drive system can also communicate an unsafe status of the pin contact with the patient's skull through an alarm, which can include both visual and audible alarms. This alarm system can alert the medical professional of any reduction of back pressure applied against the pins. Upon detection of an abnormal condition such as a decrease in back pressure of the bone against the pin, the pin drive system is capable of being automatically disabled. Early detection of a lessened back pressure on the pin and automatic stoppage of the pin drive system can protect against a pin penetration through the entire bone and potentially serious injury to the patient. Similarly, once the pins are securely in place if there is a loss or reduction of resistance or back pressure on the pin the sensors of the system can trigger an alarm to indicate a possible loosening or slippage of the skull clamp system that might permit the patient's head to move relative to the previously secured position. The skull clamp with its plurality of immobilizing pins is affixed to a 'framework that is in turn affixed to an operating table or other patient support structure such as a bed or examination table.

These and other features of the present invention are disclosed in the exemplary embodiments described in the following specification and drawings.

BRIEF DESCRIPTION OF THE DRAWING

Similar reference characters denote corresponding features consistently throughout the attached drawings.

DETAILED DESCRIPTION

Referring to the accompanying figures, the following description of exemplary embodiments of the skull clamp system, generally shown at 10, is directed to a preferred embodiment having multiple skull immobilizing pins 26; however, the number of pins 26, which can be included in the system 10 and fully provide all of the power drive and safety systems is at least one.

The skull clamp system, as shown and described in FIGS. 1-6 and the accompanying description, having power driven skull immobilizing pins 26 and a sensor safety system 62 with pressure limiting and alarm systems, provides a structure capable of absolutely immobilizing the head of a patient for medical procedures. The skull clamp system 10 also includes means for limiting the pressure applied against the bone of the skull by each of the skull immobilizing pins 26, and means for alerting medical personnel of any slippage or movement of the pins 26 relative to the skull of a patient.

Figure 1:
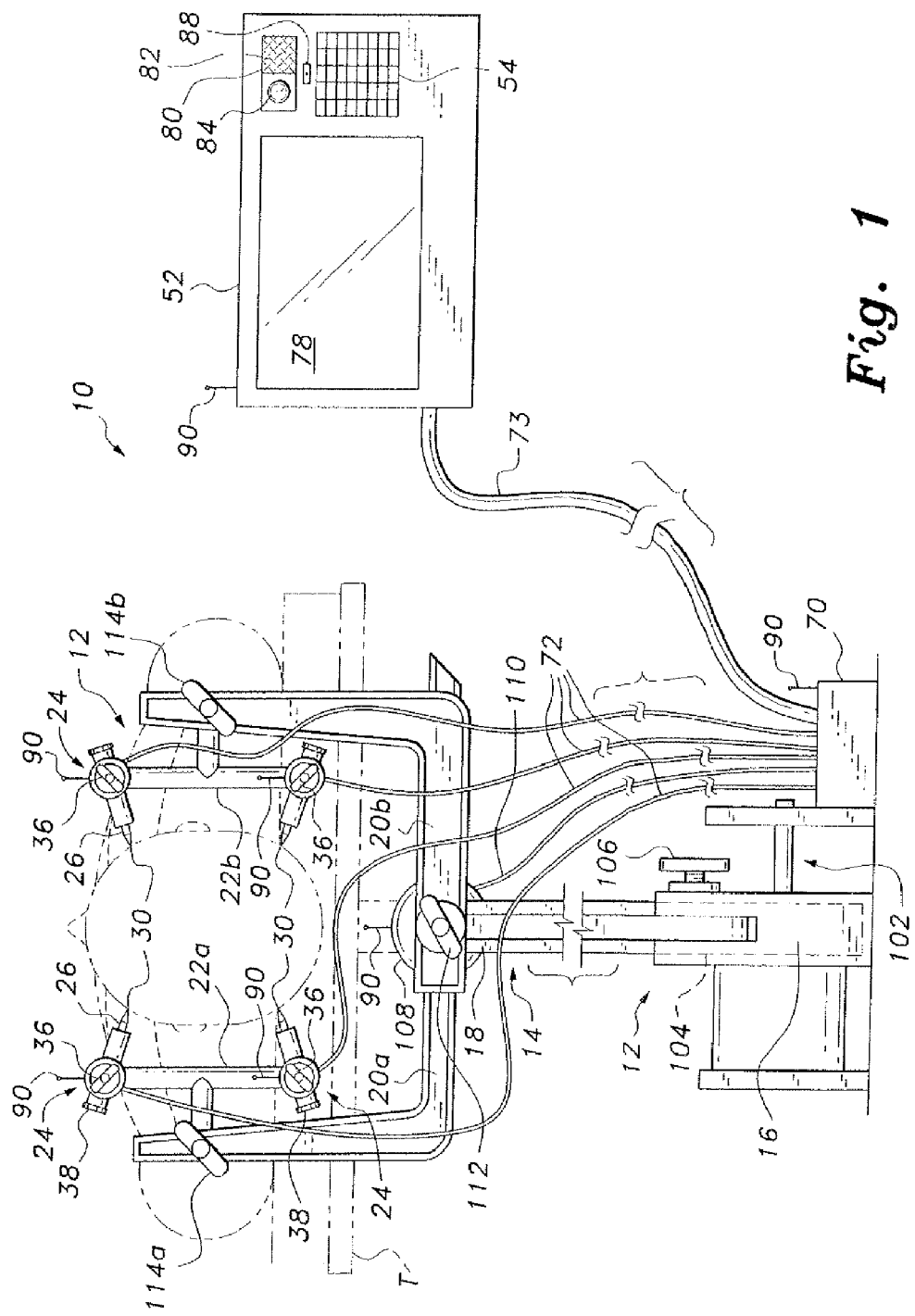
FIG. 1 is an elevation view of the skull clamp with pressure limiting and alarm systems according to the present invention, as applied to the head of a supine patient in a typical surgical position with the head extending beyond the edge of the table.
Figure 2:
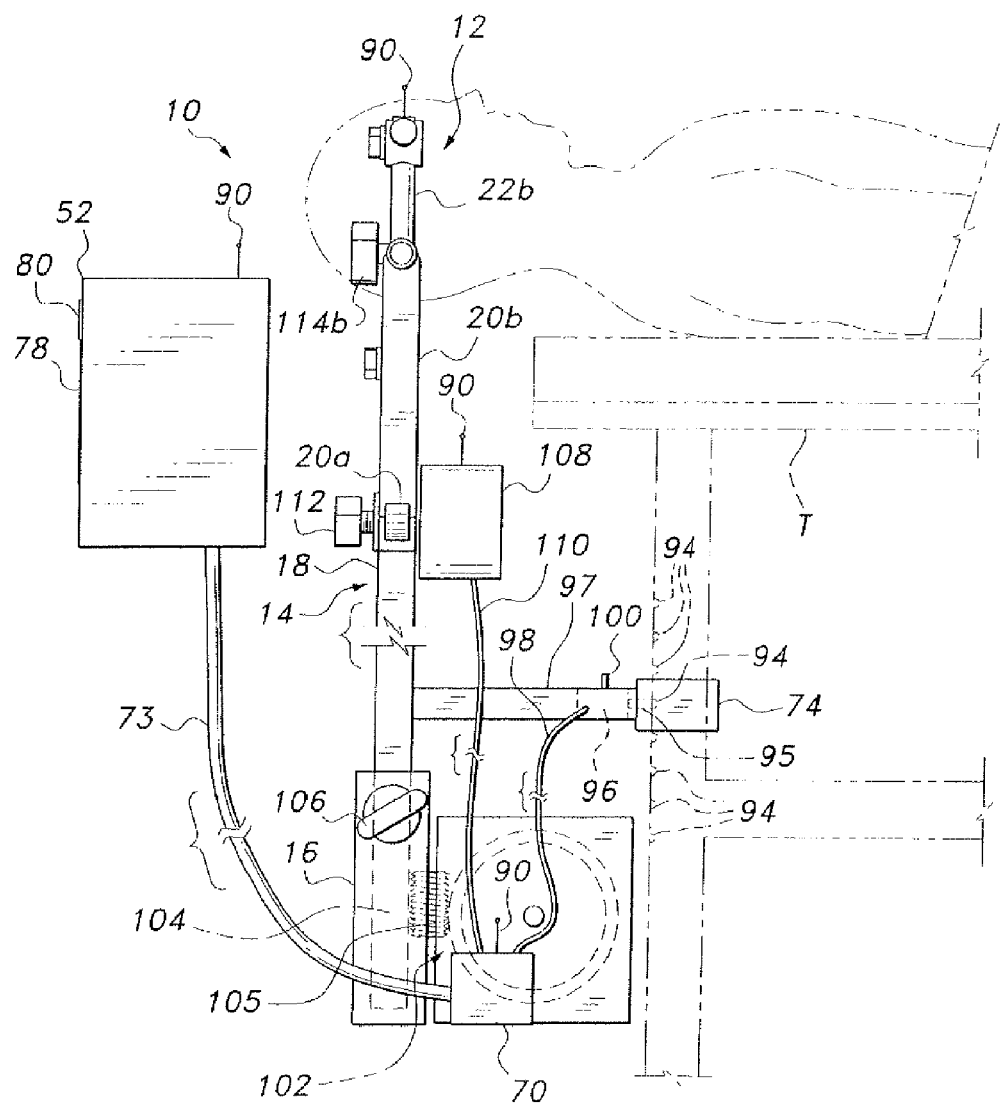
FIG. 2 is a right side elevation view of the skull clamp embodiment of FIG. 1 illustrating further details.

FIGS. 1 and 2 of the drawings illustrate a first embodiment of the skull clamp system 10 having a skull support clamp, generally shown at 12, that is adjustably connected and vertically oriented above a supporting frame, generally shown at 14. This first exemplary embodiment, wherein the skull support clamp 12 is in a substantially vertical orientation above the inferiorly connected supporting frame 14, can be used when it is advantageous for the head of the patient to extend beyond the edge of the table T, as during a neurosurgical procedure. The skull clamp system 10 can be adjustably affixed to the operating table T or other suitable structure by the vertical supporting frame 14. The two basic components of the skull clamp system 10, the skull support clamp 12 and the supporting frame 14, after being appropriately adjusted to conform to the anatomy of the patient and the needs of the surgeon, can be locked into a selected configuration relative to each other and the table T to provide a rigid and immovable skull clamp system 10 for the duration of the surgical procedure being conducted. The supporting frame 14 extends from a lower base attachment end 16 to an upper skull support attachment end 18 to which the skull support clamp 12 is adjustably attached. The skull support clamp 12 includes a first lateral arm 20a and an opposite second lateral arm 20b. The two lateral arms 20a, 20b are slidably connected and adjustable relative to one another, with the first lateral arm 20a telescoping within the second lateral arm 20b. As best seen in FIGS. 1 and 2, the distal end of the first lateral arm 20a is shown extending slightly beyond the second lateral arm 20b. Each of the lateral arms 20a, 20b respectively includes an adjustably attached first and second pin assembly mounting bracket 22a and 22b, which extend inwardly therefrom. Each of the pin assembly mounting brackets 22a, 22b includes a pair of adjustably attached skull immobilizing pin assemblies, generally shown at 24, which extend inwardly therefrom toward the skull of a patient. Each of the pin assemblies 24 includes a skull immobilizing pin 26 disposed at least partially within an outer housing 28, the distal end 66 of the pin 26 terminating in a sharpened tip 30 that is adapted to penetrate the flesh and soft tissue covering the skull and to slightly penetrate the outer layer of bone of the skull in order to provide an anchor needed to securely immobilize the skull. The sharpened tip 30 can be coated with a therapeutic compositional coating 32, such as an antibiotic composition, a blood clotting agent, or other therapeutic or prophylactic composition to support the use of the skull clamp system 10 and the safety and well-being of the patient.

Figure 4:
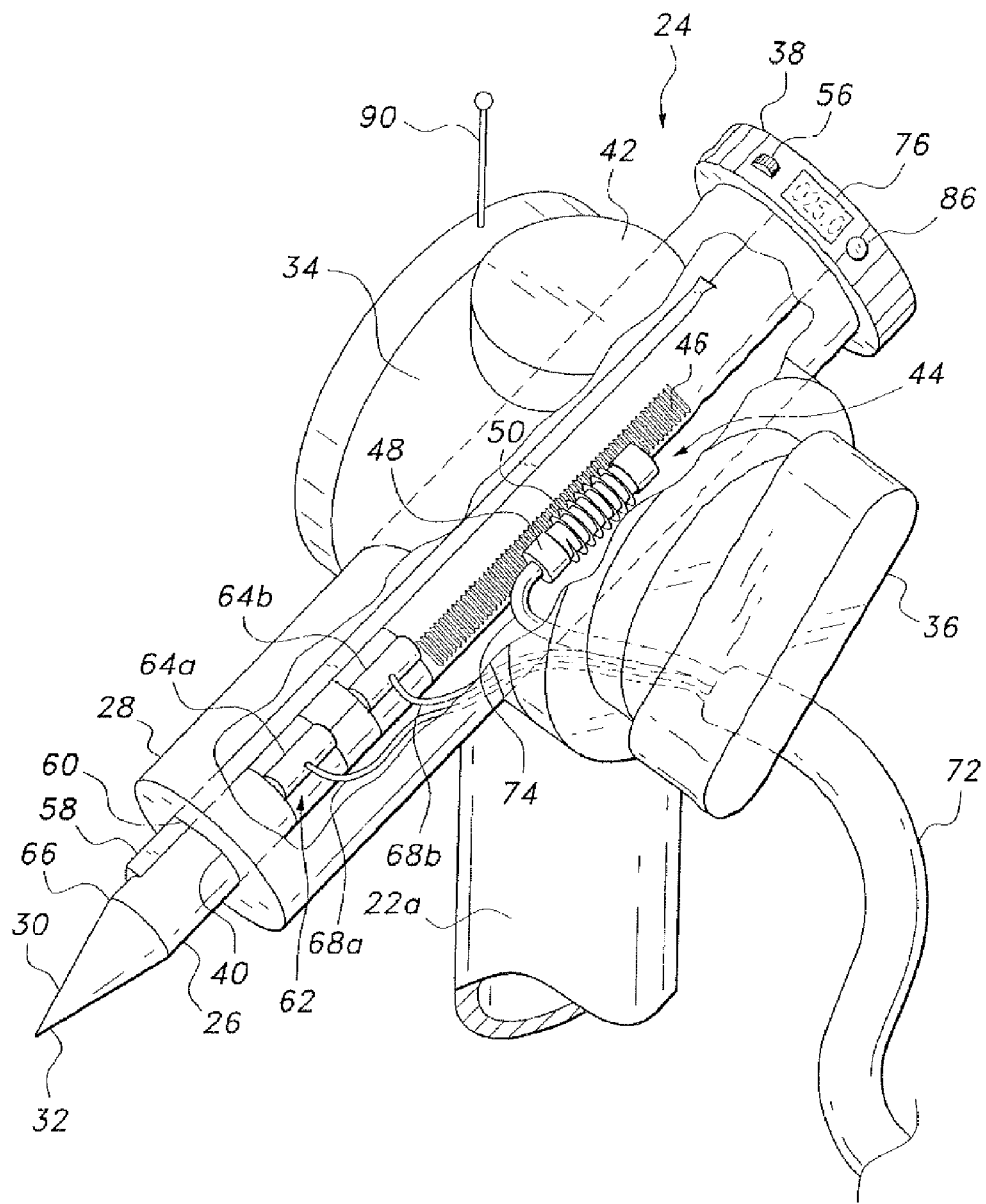
FIG. 4 is a detailed perspective view in partial section of one of the skull immobilizing pins of the skull clamp showing an exemplary linear drive system with pressure limiting and alarm systems according to the present invention.

FIG. 4 provides a detailed perspective view of one exemplary embodiment of the skull immobilizing pin assembly 24, with the outer housing 28 shown partially broken away to illustrate the interior mechanism. The pin assembly 24 of FIG. 4 is shown installed within a pin assembly holder 34, which is adjustably connected to one of the pin assembly mounting brackets 22a or 22b. The pin assembly holder 34 can be manually adjusted by a manual rotational adjustment and locking element 36. The pin assembly 24 can be provided with a manual linear adjustment control 38 to permit gross linear adjustments within a pin passage 40 defined within the pin assembly holder 34. The immobilizing pin 26, and can be selectively held immobile relative to the pin assembly holder 34 by a manually locking element 42. As shown in FIG. 4, a non-limiting example of a locking element 42 can be a locking screw actuated by a manually controlled knob.

Figure 3:
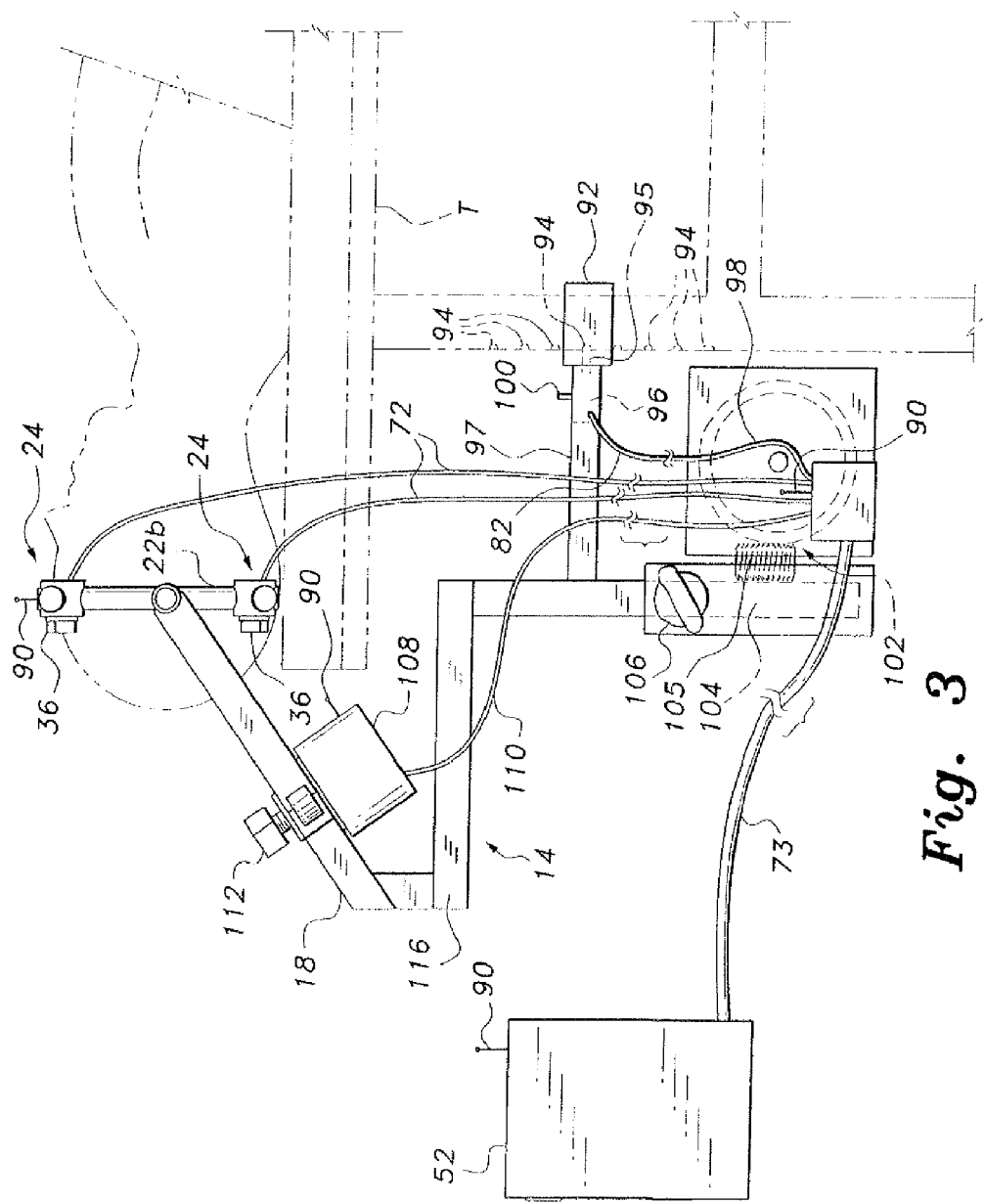
FIG. 3 is a right side elevation view of an alternative embodiment of the skull clamp with pressure limiting and alarm systems according to the present invention as applied to the head of a supine patient with the head resting on the surface of the supporting table or bed as is typical in a post-surgery or spinal fraction application.

The above-described manual adjustments, and particularly the linear adjustment feature of the immobilizing pin 26 using the manual linear adjustment control 38, are convenient for relatively coarse initial positional adjustments. Finer linear adjustment of the pin 26 is provided by the powered drive system, generally shown at 44. An electrically powered drive system is preferred and used herein for exemplary purposes; however other drive systems, such as hydraulic or pneumatic power drives, can alternatively be used. The pin 26 is linearly adjustable within its housing 28, the linear drive function being accomplished in the exemplary embodiment using an axial toothed rack 46, which is fixed on the outer surface of the pin 26 and oriented with the longitudinal axis of the pin 26 as shown in FIG. 4. An electric drive motor 48 is contained within the housing 28, with the motor 48 being capable of selectively driving a worm gear 50, which engages with the toothed rack 46 to effect fine linear drive adjustments of the pin 26. The motor 48 need not be large, as the mechanical advantage provided by the gear reduction of the worm gear 50 serves to multiply the torque output of the motor 48. A computer-controller system 52 as shown in FIGS. 1 through 3 allows the medical professional using the skull clamp system 10 to preset the degree of clamping pressure as desired via a keypad 54. As shown in the figures, wireless transmitting and receiving capability as indicated by the provision of multiple antennas for the components of the system 10 can be provided for any embodiment. The system-controller 52 is also capable of creating a time-line data recording of the pressure exerted by each of the pins 26 and automatically annotating any pressure aberrations in that recorded information.

Optionally, a manual motor controller 56 can also be provided for each pin assembly 24 to select the drive force limits that control the motor 48 and thus limit the pressure that will be automatically exerted by the linearly driven pin 26 against the skull of a patient. The pin 26 is precluded from rotating within its housing 28 by an axial key 58 that is slidably engaged with a corresponding channel 60 parallel to the longitudinal axis of the pin passage 40 defined in the body of the housing 28. By this linear drive mechanism 44, the torque of the motor 48 is converted into linear movement of the pin 26 relative to the housing 28, thereby avoiding the potential destructive effect of rotational torque to the bone of the patient's skull through contact of the tip 30 against the bone.

Figure 5:
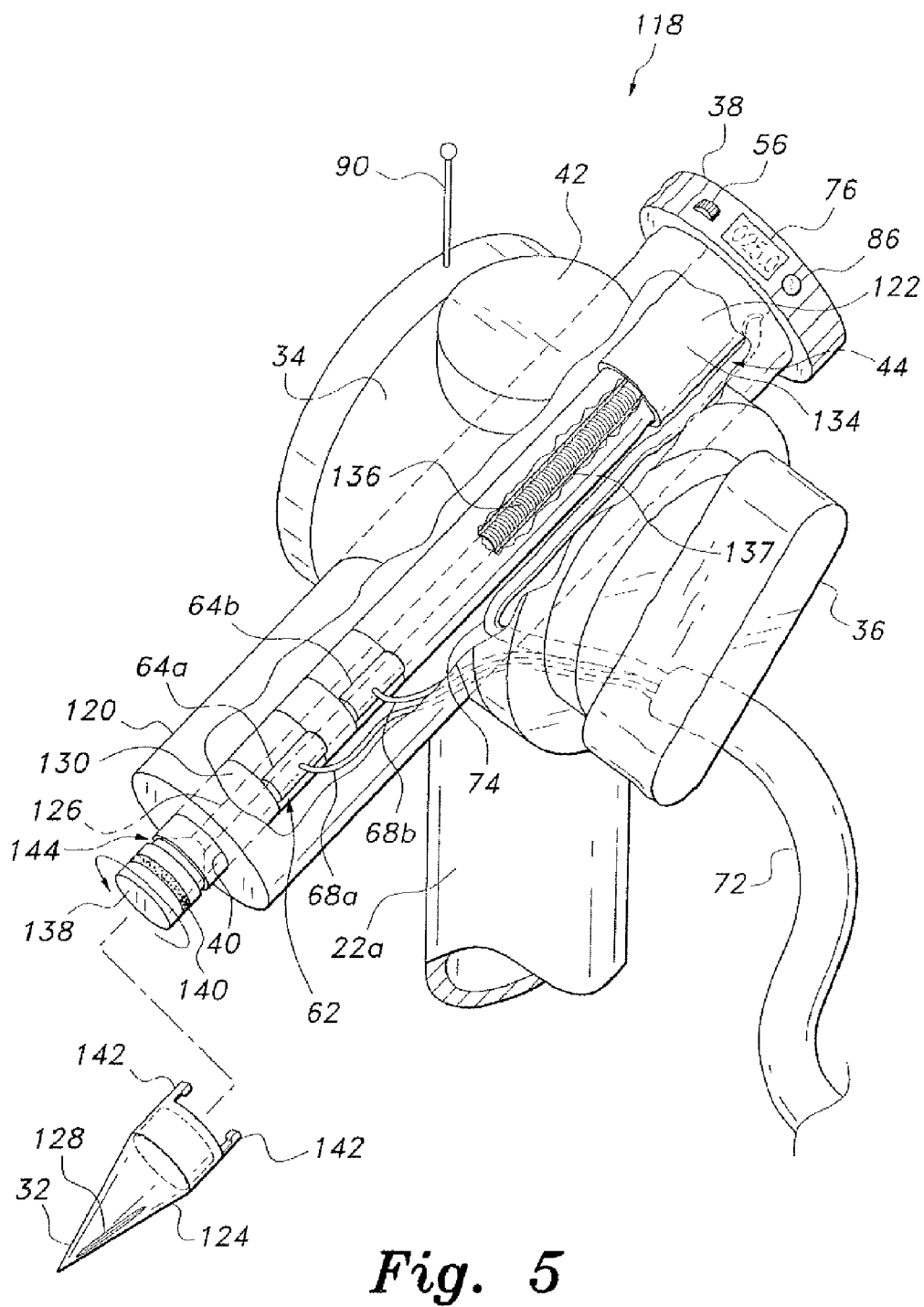
FIG. 5 is a detailed perspective view in partial section of an alternative embodiment of one of the immobilizing pins of the skull clamp, showing a rotary drive system with pressure limiting and alarm systems, wherein the rotary drive is capable of moving a detachable sharpened tip into a secure connection with the skull, the detachable sharpened tip having a freely rotatable connection with the rotating pin driven so as to enable the sharpened tip to cease rotating upon frictional contact with the skull of the patient to avoid the application of torque to the bone of the skull.

Each of the pin assemblies 24 further includes a sensor safety system, generally shown at 62, that is capable of protecting against excessive pressure or tightening of the pin 26 against the skull of a patient. As shown in FIGS. 4 and 5 the sensor safety system 62 includes a first and second sensor 64a, 64b capable of determining the degree of compression, pressure, or strain placed on the pin 26. Strain gauges are non-limiting examples of suitable sensors and will represent the sensors 64a, 64b in the remainder of the description. A solitary strain gauge 64a would be sufficient for the proper operation of the system; however, the inclusion of a second strain gauge 64b is preferred to provide the safety of redundant transmission of signals in the possible event of a single sensor/strain gauge failure. Examples of varied applications of pressure sensors or strain gauges in medical, surgical, and metal component compression, as well as strain gauges capable of producing wired and wireless signals are disclosed in U.S. Pat. No. 7,884,722 issued to Scheucher et al., U.S. Pat. No. 7,946,181 issued to Kim et al., U.S. Pat. No. 6,067,473 issued to Greeninger et al., and U.S. Pat. No. 5,168,759 issued to Bowman, each of which is fully incorporated herein by reference.

The distal portion of the pin, the tip 30, can be resiliently attached to the main portion of the pin 26, thus allowing the length of the pin 26 to compress as the pressure of the pin 26 against the bone of the skull increases due to the lineal movement of the pin 26. This compression affects both strain gauges 64a and 64b, as they are in series with one another. The safety function of providing signal redundancy from having two strain gauges 64a, 64b in series is, if one gauge fails, the remaining functional strain gauge will still sense the amount of pressure on the pin 26 and signal that the preselected limit of inward pressure of the pin 26 against the skull has been reached and power to the pin drive will be stopped. Signals are relayed from the strain gauges 64a, 64b through respective signal cables 68a, 68b to a central junction box 70 and thence on to the computer-controller system 52. The junction. Box 70 also provides electrical power to the pin drive motor 48 through a data/power cable bundle 72 that includes the signal cables 68a, 68b and corresponding power cable 74. A digital measurement of the pressure being applied against the skull by the pin 26 and sensed by the strain gauges 64a, 64b can be displayed in a pressure display 76 located with each pin assembly 24. As indicated earlier and throughout the disclosure, each of the wired information transmissions of information in the operation of the system 10 can be accomplished through wireless transmission means with provision for remote monitoring as well as continuous data recordation as desired.

The computer-controller system 52, as discussed above, is the primary means used to preset the clamping pressure of the pins 26. The degree of pressure exerted by the pins 26 can vary greatly depending upon the bone density and/or skull structure of the patient. Pressure developed against the skull by each of the pin assemblies 24 can be displayed on the monitor screen 78 in a single location, as well as being visible on the pressure display 76 of each pin assembly 24, as noted above. In the event that some anomaly is sensed by the sensor safety system 62, e.g., a sudden decrease in pressure sensed by the strain gauges 64a and 64b that could indicate that the pin 26 is suddenly meeting with too little resistance due to an imminent break through or fracture of the skull by the advancing pin 26, the sensor safety system 62 will shut down electrical power to the pin drive motor 48 and simultaneously trigger the alarm system 80 to provide an audible alert via a speaker 82 and/or a visual alert such as a light 84 on the computer-controller system 52. A pin fault indicator light 86 can also be prominently positioned on each pin assembly 24 to inform the surgical team which of the pin assemblies triggered the alarm system 80. A safety system reset control 88, such as a button or switch, can also be provided in the event of a safety system false alarm being transmitted. The computer-controller system 52 communicates with the junction box 70 through a cable included in the data/power cable bundle 73. Alternatively, the sensor safety system 62 can be monitored and/or controlled along with all other data transmission remotely by the computer-controller system 52 through a wireless communication system, as indicated by the provision of transmitting and receiving antennae 90 shown in FIGS. 1 through 5 for all major components of the system 10.

Additional mechanical and positional adjustment can be provided for the skull clamp system 10, as desired. The embodiment shown in FIGS. 1 and 2 is adjustably attached to the table T by a selectively adjustable clamp 92, as shown in FIGS. 2 and 3. The table T includes a series of height adjustment locks 94 defined therein, into which a lock pin 95 can be releasably inserted. The lock pin 95 is actuated by a power lock 96, for example, a solenoid actuator that can be included or attached to the table attachment arm 97 of the support frame 14; with the power lock 96 receiving power and control through the lock power cable 98 extending from the junction box 70. Alternatively, a manual locking device 100, such as a handle or lever, can be provided for locking and releasing the lock pin 95. The alternative embodiment of FIG. 3 utilizes the same system for table attachment and coarse vertical adjustment.

The above-described height adjustment for the skull clamp system 10 provides only relatively coarse adjustment for the height of the skull support clamp 12. Finer vertical adjustment can be provided by a vertical power drive mechanism, generally shown at 102, that can be installed at the base of the adjustable vertical column 104 of the supporting frame 14. As shown in FIG. 2 and FIG. 3 the vertical power drive mechanism 102 can preferably be provided as a worm drive 105 that can selectively advance or retract the adjustable vertical column 104 as desired, although any mechanized drive system can be used. A vertical manual lock 106 can be provided to releasably secure the height adjustment of the skull clamp system 10 at a desired position. A powered tilt actuator 108 can be provided at the skull support attachment end 18 of the supporting frame 14. Preferably, and as shown in the example described herein, the powered tilt actuator 108 can be an electrical motor; however, any alternative power source such as hydraulic or pneumatic power can be employed. The power tilt actuator 108 can be capable of adjustably rotating the system lateral arms 20*a*, 20*b* to orient them as desired. The power tilt actuator 108 receives its power through a tilt motor cable 110 extending from the junction box 70. A manually actuated tilt lock 112 can be provided at the juncture of the two lateral arms 20*a*, 20*b* with the skull support attachment end 18 of the supporting frame 14. Finally, the pin assembly mounting brackets 22*a*, 22*b* can be adjusted relative to their respective lateral arms 20*a*, 20*b*, with manual bracket locks 114*a*, 114*b* that are provided for each of the pin assembly mounting brackets 22*a* and their corresponding lateral arms 20*a*, 20*b*.

FIG. 3 of the drawings illustrates an alternative embodiment, wherein the skull support attachment end 18 of the supporting frame 14 is provided with an offset arm 116 that serves to offset the skull support attachment end 18 sufficiently to clear the head end of the table T when the head of the patient is resting thereon. It will be seen that the rest of this alternative embodiment of the system 10 is essentially identical to that of FIGS. 1 and 2, including the various manual and power assisted adjustment and locking means. This particular embodiment of the invention, which is configured to permit the patient's head to rest on the table surface is particularly advantageous for post-surgery or neck injury patients that require the head be held in place for further treatment such as for example spinal traction. For such patients it is possible that Magnetic Resonance Imaging (MRI) procedures may be required. For that eventuality, all embodiments of the skull clamp system 10, in addition to conventional metallic construction, can alternatively he manufactured of non-ferromagnetic materials, such as but not limited to titanium, polymeric, carbon fiber or other composite materials, so as to permit the use of the system 10 during an MRI procedure on the patient. Identical reference characters are used for identical components between the first embodiment of FIGS. 1 and 2, and the alternative embodiment illustrated in FIG. 3.

FIG. 5 shows a detailed perspective view of an alternative pin assembly, generally shown at 118, with an alternative outer housing 120 shown partially broken away to illustrate the interior mechanism. The general structure and function of this alternative embodiment of a pin assembly 118 is very similar to that of the primary embodiment of the pin assembly 24 shown in FIG. 4 and earlier described in detail. The primary distinctions between the primary embodiment pin assembly 24 of FIG. 4 and the alternative pin assembly 118 of FIG. 5 is the use of an alternative outer housing 120 that does not require an axial key 58 or corresponding channel 60 as shown in the first described embodiment of FIG. 4 and the use of an alternative rotary drive system 122 in the alternative pin assembly 118 rather than a linear drive system, generally shown at 44 in the first described non-rotating pin assembly 24 of FIG. 4. Additionally, the alternative pin assembly 118 of FIG. 5 includes the feature of an alternative pin 126 rotatably mounted within the lumen of a stationary shaft 130 that is fixedly disposed within at least a portion of the alternative outer housing 120. The distal end 138 of the rotatable pin 126 terminates in a freely rotatable connection to a torqueless, sharpened, detachable tip 124. The rotatable pin 126 extends inwardly from the detachable tip 124 located outside of the distal end of the alternative outer housing 120 into the lumen of the stationary shaft 130, which is fixedly disposed within and along the longitudinal axis of the alternative outer housing 120. Mounted on the proximal end 132 of the outer stationary shaft is a rotational drive motor 134 that is connected to a rotating, threaded drive shaft 136, which is threadably engaged with at least a proximal portion of the lumen of the stationary shaft 130. When activated under the control of the computer-controller system 52, the rotational drive motor 134 causes the rotating, threaded drive shaft 136 to rotate so as to threadably interact with the complimentarily threaded inner wall 137 of the lumen of the stationary shaft 130 resulting in a linear movement of the rotatable pin 126 outward from within the alternative outer housing 120 to effect forcible contact of the detachable tip 124 positioned at the distal end 138 of the rotatable pin 126 against the outer portion of the skull of a patient. The freely rotationally connected, sharpened, detachable tip 124 is designed to make contact with and slightly penetrate the outer layer of bone of a patient's skull as a result of the pressure or force applied by the proximally directed movement of the rotatable pin 126. The releasable, freely rotating connection of the detachable tip 124 to the rotatable pin 126 can include a pin bearing 140 to minimize frictional forces between the rotatable pin 126 and the freely rotating detachable tip 124. As shown in FIG. 5, the releasable, freely rotational connection of the detachable tip 124 can be provided by grasping arms 142 movably interacting with a holding groove 144 and the rotational connection being facilitated by a low-friction circumferentially disposed pin bearing 140. For illustration, the circumferentially disposed pin bearing 140 can be a Teflon™ bearing or the like; however any bearing design or material as well as any releasable connection between the rotatable pin 126 and the detachable tip 124 can be used in this alternative embodiment and remain within the scope of the invention. Other non-limiting examples of releasable connections and bearings can include for example snap fit, bayonet fit, or similar connections can be employed with lubricant, ball bearing, or other means of reducing friction between the two rotatably connected elements of the pin and the detachable tip. In operation, the rotatable pin 126, as it is extended distally from the alternative outer housing 120 by the driving force of the rotational drive motor 134, will force the detachable tip 124 against the outer surface of the patient's skull. The detachable tip 124 can be provided with one or more surface frictional elements 128 that are disposed on the tip's surface for the purpose of impeding any rotation of the detachable tip 124 after it makes contact with the patient's skin or bone. Upon contact with the patient's skull, the frictional forces of the tissue and bone against the detachable tip 124 with its surface frictional elements 128 will act to slow and stop the detachable tip 124 from continuing to rotating in concert with the rotatable pin 126 thereby avoiding the transmission of potentially destructive rotational forces from the rotatable pin 126 to the bone of the patient's skull. The freely rotatable connection of the detachable tip 124, aided by the friction reducing function of the pin bearing 140, will allow the rotatable pin 126 to continue to forcibly rotate in response to the driving force of the rotational drive motor 134 without transmitting that potentially bone damaging rotational torque to the underlying bone being securely held by the detachable tip 124. Beyond the primary benefit of avoiding the transmission of potentially destructive torque forces to the bone, the freely rotatable, detachable tip 124 also provides the advantage of rendering the detachable tip 124 to be a disposable and easily replaced element of the head clamp system 10 after it has been used and potentially contaminated by contact with the blood and tissue of the patient.

It is within the concept of the invention that the configuration and features of the detachable tip 124 and distal end of the rotatable pin 126 can be adapted to detachably connect to the earlier described embodiment having a non-rotating pin that is driven by a linear system 44, as shown in FIG. 4. The ease of adapting the detachable tip 124 to the linearly driven pin 26 of the linear drive system embodiment of FIG. 4 shows that a detachable tip and therefore a disposable tip can be provided for any embodiment of the skull clamp system 10.

Figure 6:
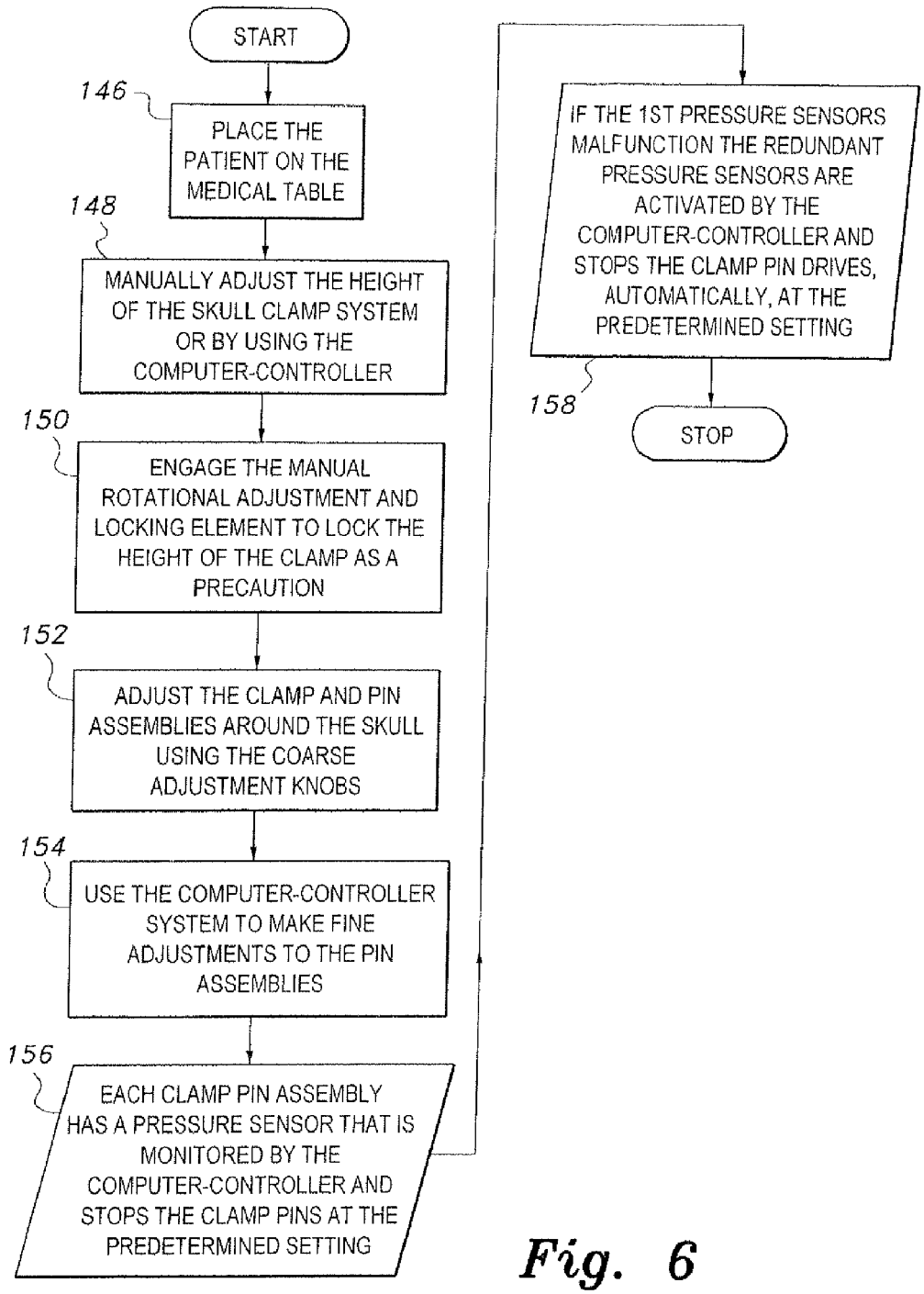
FIG. 6 is a flowchart describing the basic steps in the procedure for setting up and operating the skull clamp with pressure limiting and alarm systems according to the present invention.

FIG. 6 of the drawings is a flow chart briefly describing the basic steps involved in the use of the skull clamp system 10. Initially the patient is placed upon the operating or medical treatment table T, as indicated by the first step 146 of FIG. 6. In the second step 148, the height of the skull clamp system 10, which includes the two lateral arms 20a, 20b, the pin assembly mounting brackets 22a, 22b, and the pin assemblies 24, can be initially adjusted manually or by entering position instructions through the computer-controller system 52. In the third step 150 after gross adjustments have been made the clamp system 10 can be locked into position using the manual rotational adjustment and locking element 36. The tilt of the lateral arms 20a, 20b and pin assemblies 24 can be manually adjusted and secured at this time as well.

When the above adjustments to the device configuration have been completed, the pin assemblies 24 can then be manually adjusted to make contact with the patient's head by means of the manual rotational adjustment and locking element 36 and manual linear adjustment control 38 for each pin assembly 24 as indicated by the fourth step 152 in FIG. 6. The computer-controller system 52 is then used to make the final, fine adjustments of each of the pin assemblies 24, as indicated by the fifth step 154 of FIG. 6. As noted in the sixth step 156 of FIG. 6, and as shown in embodiments of FIGS. 4 and 5 each of the pin assemblies 24 includes at least one sensor or strain gauge 64a, 64b that communicates with the computer-controller system 52 to limit the pressure applied by the linear drive motor 48 in FIG. 4 or alternatively the rotational drive motor 134 in FIG. 5 of each disclosed embodiment of the skull clamp system 10. When the preselected pressure limit is reached, the strain gauges 64a, 64b signal the computer-controller system 52, which immediately responds by shutting down the power to the linear drive motor 48 (FIG. 4) or alternatively to the rotational drive motor 134 (FIG. 5) to stop the advance of the respective pin 26 (FIG. 4) or rotatable pin 126 (FIG. 5). With two such sensors or strain gauges 64a, 64b, if the one of the strain gauges 64a, 64b malfunctions or fails to signal the computer-controller system 52, the remaining or redundant sensor will send the appropriate signal and the computer-controller system 52 will shut down the power to the pin drive motor 48 (FIG. 4) or 134 (FIG. 5), thus precluding excessive advance of the pin 26 (FIG. 4) or rotatable 126 (FIG. 5) and possibly life-threatening injury to the patient. This procedure is indicated in FIG. 6 as the seventh step 158.

It is to be understood that the present invention is not limited to the embodiments described above, but encompasses any and all embodiments within the scope of the following claims.

What is claimed:

1. A skull clamp system, comprising:
 a skull clamp support having:
  at least one pin, the pin having a distal end, a proximal end, and a central portion disposed therebetween, the distal end being configured to contact the bone of a patient's skull; and
  a support clamp connected to the at least one pin;
  a powered drive system connected to the pin, the powered drive system being capable of driving the pin into contact with the bone of a patient's skull, and
  at least one sensor in proximity with said pin, the at least one sensor being configured for sensing the degree of back pressure resulting from contact of said pin against the skull of the patient.

2. The skull clamp system of claim 1, wherein the at least one sensor is capable of transmitting a signal to a computer-controller system, the signal indicating the degree of back pressure on said pin that is sensed as said pin is driven against the bone of the patient's skull.

3. The skull clamp system of claim 1, wherein the at least one sensor comprises multiple sensors, the multiple sensors being capable of independently providing the signal indicating the degree of back pressure on said pin.

4. The skull clamp system of claim 1, further comprising an alarm system connected to the at least one sensor, the alarm system having means for initiating an alarm signal indicating an unsafe degree of back pressure on said at least one pin.

5. The skull clamp system of claim 4, wherein said alarm signal comprises at least one alarm signal selected from the group consisting of visual and audible alarms.

6. The skull clamp system of claim 1, wherein said powered drive comprises a motor driven by a power source selected from the group consisting of electrical, pneumatic, and hydraulic power sources.

7. The skull clamp system of claim 1, wherein said powered drive system is a drive system selected from the group consisting of a linear drive system and a rotary drive system.

8. The skull clamp system of claim 1, wherein said pin has a detachable tip at the distal end.

9. The skull clamp system of claim 1, wherein said pin has a tip rotatably connected to the distal end of said pin.

\* \* \* \* \*